(12) United States Patent
Fein et al.

(10) Patent No.: US 8,546,341 B2
(45) Date of Patent: Oct. 1, 2013

(54) COMPOSITIONS AND METHODS FOR TREATING BRUISES

(75) Inventors: Howard Fein, Rolling Hills Estates, CA (US); Mindy B. Berlin, Delray Beach, FL (US)

(73) Assignee: M. Alphabet, LLC, Deerfield Beach, FL (US)

( * ) Notice: Subject to any disclaimer, the term of this patent is extended or adjusted under 35 U.S.C. 154(b) by 0 days.

(21) Appl. No.: 13/036,279

(22) Filed: Feb. 28, 2011

(65) Prior Publication Data
US 2011/0293696 A1   Dec. 1, 2011

Related U.S. Application Data

(60) Provisional application No. 61/349,335, filed on May 28, 2010, provisional application No. 61/364,033, filed on Jul. 14, 2010.

(51) Int. Cl.
| | |
|---|---|
| A61K 31/7048 | (2006.01) |
| A61K 31/35 | (2006.01) |
| A61K 31/70 | (2006.01) |
| A61K 31/375 | (2006.01) |
| A61K 9/12 | (2006.01) |
| A61K 36/00 | (2006.01) |

(52) U.S. Cl.
USPC .......................................... 514/27; 424/736

(58) Field of Classification Search
None
See application file for complete search history.

(56) References Cited

U.S. PATENT DOCUMENTS

| | | | |
|---|---|---|---|
| 5,474,782 A | 12/1995 | Winter et al. | |
| 5,626,883 A | 5/1997 | Paul | |
| 5,804,168 A * | 9/1998 | Murad | 424/59 |
| 5,997,875 A | 12/1999 | Zhou et al. | |
| 6,203,818 B1 * | 3/2001 | Vester | 424/569 |
| 6,224,872 B1 | 5/2001 | Shibuya et al. | |
| 6,541,447 B1 | 4/2003 | Dawson | |
| 6,596,761 B2 | 7/2003 | Lanzendorfer et al. | |
| 2004/0034098 A1 | 2/2004 | Varani et al. | |
| 2004/0087516 A1 * | 5/2004 | Rosenbloom | 514/27 |
| 2004/0131579 A1 | 7/2004 | Duraiswami et al. | |
| 2005/0129787 A1 | 6/2005 | Murad | |
| 2006/0029587 A1 * | 2/2006 | Lane | 424/94.1 |
| 2006/0067959 A1 * | 3/2006 | Nimni et al. | 424/401 |
| 2006/0134095 A1 | 6/2006 | Ito | |
| 2007/0053960 A1 | 3/2007 | Brown et al. | |
| 2007/0292493 A1 * | 12/2007 | Brierre | 424/449 |
| 2008/0044364 A1 * | 2/2008 | Carola et al. | 424/59 |
| 2008/0045478 A1 | 2/2008 | Buchholz et al. | |
| 2008/0057138 A1 | 3/2008 | Telford et al. | |
| 2009/0028930 A1 | 1/2009 | Cranner et al. | |
| 2009/0081285 A1 * | 3/2009 | Golz-Berner et al. | 424/451 |
| 2009/0104292 A1 | 4/2009 | Alam | |
| 2009/0130027 A1 | 5/2009 | Shanler | |
| 2009/0246153 A1 | 10/2009 | Kern | |
| 2010/0104673 A1 | 4/2010 | Tecco | |
| 2010/0124549 A1 * | 5/2010 | Studin | 424/94.65 |

FOREIGN PATENT DOCUMENTS

| | | | |
|---|---|---|---|
| JP | 05186344 A * | 7/1993 | |
| WO | WO2009073612 | 6/2009 | |

OTHER PUBLICATIONS

Yoshiaki Miyake, Kanefumi Yamamoto, and Toshihiko Osawa. Isolation of Eriocitrin (Eriodictyol 7-rutinoside) from Lemon Fruit (*Citrus limon* Burm. f.) and Its Antioxidative Activity. Food Sci Technol Int Tokyo. 3 (1),84-89. 1997.*
S. Batkin, S. J. Taussig, and J. Szekerezes. Antimetastatic effect of bromelain with or without its proteolytic and anticoagulant activity. J Cancer Res Clin Oncol (1988) 114:507-508.*
Web page for Mephyton, downloaded from the internet on Apr. 25, 2013 from the site: http://www.mephyton.com/.*
Andrew Bebbington, Rohit Kulkarni, and Paul Roberts. Case Report: *Ginkgo biloba* Persistent Bleeding After Total Hip Arthroplasty Caused by Herbal Self-Medication. The Journal of Arthroplasty vol. 20 No. 1 2005, pp. 125-126.*
AK Presnell, Scurvy and Blood Coagulation, Nutrition Reviews, vol. 18, No. 8, 1960, pp. 242-244.*
E. Ernst. Efficacy of Homeopathic *Arnica*: A Systematic Review of Placebo-Controlled Trials. Arch Surgery, vol. 133, Nov. 1995. pp. 1187-1190.*
Shanno, RL, The American Journal of the Medical Sciences, May 1946, p. 539-543, vol. 211(5).
Saelhof, CC, American Journal of Digestive Diseases, Jul. 1955, p. 204-206, vol. 22.
Pace-Asciak, CR, et al., Clinics Chimica Acta, Mar. 1995, p. 207-219, vol. 235(2).
Dunphy et al., 144 Annals of Surgery, Sep. 1956, p. 304-316.
Macedo SB, et al., Homeopathy, Apr. 2004, p. 84-7, vol. 93(2).
Richer, S. Journal of American Optometric Association, 1996, p. 30-49, vol. 67.

(Continued)

*Primary Examiner* — Frederick Krass
*Assistant Examiner* — Michael P Cohen
(74) *Attorney, Agent, or Firm* — Duane Morris, LLP; Lee Crews

(57) ABSTRACT

A composition for the treatment of bruising is disclosed. The composition can include an antioxidant, one or more citrus flavanoids, as active agents along with a pharmaceutically acceptable excipient or filler. The compositions are nutriceutical formulations having the capacity to reduce the number of bruises that occur over time and that reduce the healing time of bruises. The compositions are preferably in tablet form for oral consumption one or more times per day. A method of reducing bruising is also disclosed in which a patient in need of a treatment for bruising or at risk of developing bruises is identified. The composition can then be administered orally to the patient.

13 Claims, 3 Drawing Sheets

(56) References Cited

OTHER PUBLICATIONS

Kotlus, BS et al., Ophthalamic Plastic and Resconstructive Surgery, 2010, p. 395-7, vol. 26(6).
Totonchi A and Guyuron B, Plastic and Reconstructive Surgery, 2007, p. 271-4, vol. 120(1).
Stevinson C, et al., Journal of the Royal Society of Medicine, 2003, p. 60-5, vol. 96(2).
Ernst E and Pittler MH, Archives of Surgery, 1998, p. 1187-90, vol. 133(11).
Reinhold et al., 41 J. American Academy of Dermatology, 207-208 (1999).
Pearson et al., 164 JAMA, 1675-1678 (1957).
Leu et al., 163 British J. of Dermatology, 557-563 (2010).
Dinehart et al., 31 Dermatologic Surgery, 819-826 (2005).
International Search Report and Written Opinion for International Patent App. No. PCT/US11/26425.

* cited by examiner

COMPOSITIONS AND METHODS FOR TREATING BRUISES

BACKGROUND

Solar purpura also known as actinic purpura and Bateman's senile purpura is a skin condition characterized by large, sharply outlined, 1 to 5 cm, dark purplish-red subcutaneous hematomas or bruises. The condition is characterized by recurrent bruising on sun-exposed areas which most commonly appear on the arms, hands, shins and the face. The bruises develop in the absence of trauma. New bruises can develop every few days.

The condition is most common in elderly individuals and is thought to be caused by sun-induced damage to the connective tissue of the skin. It affects about 8-12 million people in the United States. Worldwide it is believed that between 16 to 30 million individuals over the age of 50 will suffer from the disease in 2011 and its prevalence will increase in the future.

No treatment for solar purpura currently exists. Lesions typically fade and disappear over a period of up to 3 weeks in the absence of treatment. However, the lesions can be emotionally distressing to patients because of the cosmetic disfigurement of the skin. Such treatments will also be useful in the treatment of bruising in general.

SUMMARY

A composition for the treatment of bruising is disclosed. The composition can include an antioxidant, one or more citrus flavanoids, as active agents along with a pharmaceutically acceptable excipient or filler. The compositions are nutraceutical formulations having the capacity to reduce the number of bruises that occur over time and the capacity to reduce the healing time of bruises. The compositions are preferably in tablet form for oral consumption one or more times per day. A method of reducing bruising is also disclosed in which a patient in need of a treatment for bruising or at risk of developing bruises is identified and the composition is then administered orally to the patient.

Additional features and advantages are described herein, and will be apparent from, the following Detailed Description.

DETAILED DESCRIPTION

Figure 1:
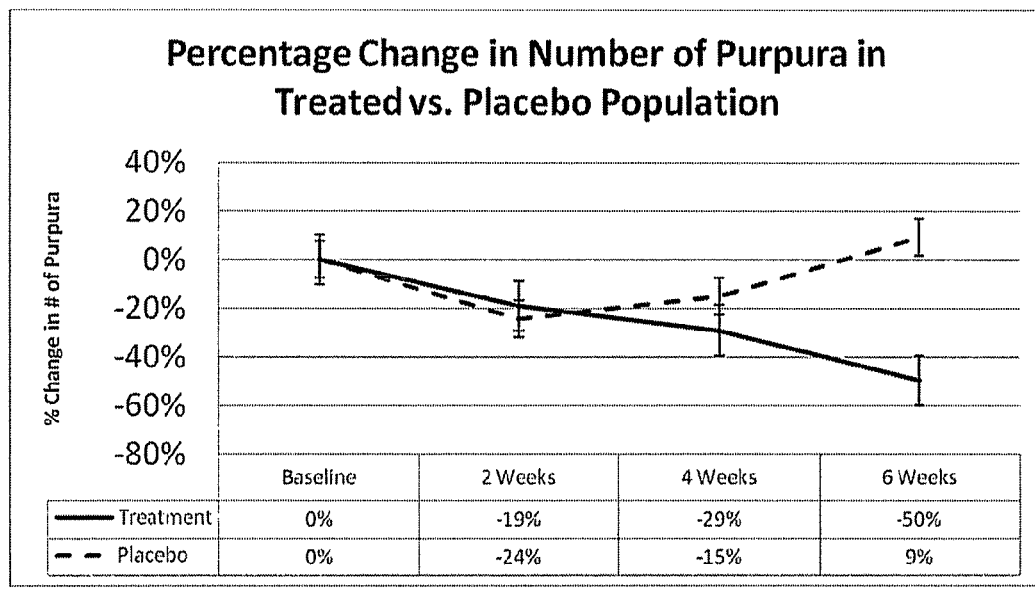
FIG. 1 shows the percent change from baseline in the number of purpura lesions at each treatment interval for both the treatment and placebo groups.

A composition for the treatment of bruising is disclosed. Active agents in the composition will preferably be capable of eliciting one or more of the following effects in humans, including enhancing circulation, increasing the strength of a patient's blood vessels and/or capillaries, reducing platelet aggregation, accelerating capillary repair, increasing collagen synthesis, decreasing capillary permeability, or reducing tissue edema. Ingredients that increase the speed of clearance of leaked blood can also be used. The active agents can include an antioxidant, one or more citrus flavanoids.

Many antioxidants are known and can be used in the composition however, ascorbic acid and its derivatives can be used. Derivatives of ascorbic acid that may find use include its water soluble esters such as ascorbyl phosphate. Lipophilic esters such as ascorbyl palmitate and ascorbyl tetra-isopalmitoyl can also be used. Ascorbic acid is preferred.

Many citrus flavanoids are known and are suitable for use in the present compositions so long as the resulting composition has the ability to increase the speed of healing of bruises or to reduce the appearance of bruises. For example, citrus flavanoids such as hesperidin, rutin, eriocitrin, and the like can be used. Mixtures of such flavanoids can also be used.

A variety of other ingredients can also be included in the compositions as long as they do not interfere with the therapeutic use of the composition in the treatment or prevention of bruising. For example, certain compositions can contain calcium carbonate, calcium ascorbate, an extract of *Arnica montana*, vitamin K, folic acid, *Croton lechleri* extract, *Aspilia africana* extract, or a combination of these ingredients.

Preferably, the ingredients are readily available for example from commercial sources. For example, certain dietary supplements having one or more of the above characteristics can be used. Ideally the ingredients will have been proven safe through use. For example, ingredients that have been in use for more than 10 years, more preferably 20 years or even 70 years or longer, such as over-the-counter nutritional products can be used.

In one embodiment the composition includes the following ingredients, ascorbic acid, rutin, citrus bioflavinoids, hesperidin, eriocitrin, and *Arnica montana*. This combination of active agents has the unexpected characteristic of providing synergistic bruise healing.

Suitable formulations can include from about 100 mg to about 1,000 mg of ascorbic acid; from about 1 mg to about 2,000 mg of rutin, from about 1 mg to about 2,000 mg of one or more citrus bioflavinoids, from about 1 mg to about 2,000 mg of eriocitrin, from about 0.5 mg to about 10 mg of *Arnica montana*, and from about 100 mg to about 2,000 mg of calcium, for example.

The compositions can be used to prevent and to speed the healing of bruising. Bruising that may be treated in this manner includes bruising caused by senile purpura, vasculitis, hemophilia, a coagulation disorder, von Willebrand's disease, Factor V Leiden deficiency, capillaritis, pigmented purpuric dermatosis, Schamberg's disease, sun damage, trauma, surgery, cosmetic procedures, anticoagulant medication, photo aging, Ehlers-Danlos Syndrome, a connective tissue disorder and the like.

The disclosed compositions can also include one or more pharmaceutically acceptable excipients, which, as used herein, includes solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, 18th Edition, Part 8 discloses various carriers used in formulating pharmaceutical compositions and known techniques for the preparation thereof. Except insofar as any conventional carrier medium is incompatible with the selected active agents, such as by producing any undesirable biological effect or otherwise interacting in a deleterious manner with any other component(s) of the pharmaceutical composition, it can be used in the present compositions.

Some examples of materials which can serve as pharmaceutically acceptable excipients include, but are not limited to, sugars such as lactose, glucose and sucrose; starches such as corn starch and potato starch; cellulose and its derivatives such as sodium carboxymethyl cellulose; ethyl cellulose and cellulose acetate; powdered tragacanth; malt; gelatin; talc; excipients such as cocoa butter and suppository waxes; oils such as peanut oil; cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents and preservatives.

The disclosed compositions can be administered by any route of administration including orally into the digestive tract as by swallowing a tablet; orally buccal, sublingual or sublabial as by disintegrating tablet or chewing gum or an oral spray; orally by inhalation into the respiratory tract; ocular or nasal as by drops, ointments or hydrogels, through the urogenital tract intravesicularly or intravaginally, rectally, dermally as by ointments or transdermal patches, or by injection into the skin, muscle tissue, or organs as appropriate. Oral administration is preferred. Certain administration methods, include the step of administering the composition orally one or more times a day, to obtain the desired therapeutic effect.

Liquid dosage forms for oral administration are contemplated and pharmaceutically acceptable emulsions, microemulsions, solutions, suspensions, syrups and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Conventional nutriceutical procedures can be employed to create liquid drinks, powder mixes or food-stuffs comprising the ingredients.

Compositions for rectal or vaginal administration are preferably suppositories which can be prepared by mixing the selected active agents with suitable non-irritating excipients or carriers such as cocoa butter, polyethylene glycol or a suppository wax which are solid at ambient temperature but liquid at body temperature and therefore melt in the rectum or vaginal cavity to release the active agent.

The disclosed compositions are particularly useful when incorporated into tablets or capsules however, dragees, pills, powders, and granules are also contemplated. Known procedures conventionally employed by the pharmaceutical industry may be used to produce such compositions with the disclosed active agents. In such solid dosage forms, the active agents can be mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. The dosage form may also comprise buffering agents.

Tablets can be formed by mixing the ingredients with a binder which is used to impart cohesive qualities to a tablet formulation, and thus ensure that the tablet remains intact after compaction. Suitable binders include, but are not limited to, starches such as pregelatinized maize starch, alginates, gelatin, carboxymethylcellulose, sugars (for example, sucrose, glucose, dextrose, and maltodextrin), waxes, natural and synthetic gums, polyvinylpyrrolidone (PVP), and cellulosic polymers (for example, microcrystalline cellulose, hydroxypropyl cellulose, hydroxypropyl methylcellulose, methyl cellulose, and hydroxyethyl cellulose).

Under certain circumstances there is a requirement for fast disintegrating or dissolving tablets which can be administered even without water. Such fast dissolving tablets disperse readily to form a suspension or solution of the active agents after mixing with the saliva, which is easily swallowed by the patients. These are particularly suitable for children or aged patients who have difficulty in chewing and/or swallowing an intact tablet/capsule. Fast mouth dissolving tablets are also suitable for patients suffering from nausea or vomiting; who have an upper gastrointestinal tract disease e.g., injury in food pipe; who have undergone upper GI surgery; who are prostrate; who are elderly and have frequent urination problems at night; who are incapacitated elderly patients e.g. suffering from Parkinson's disease, who are in a situation where water is not available.

Fast dissolving tablets can be formed from the active agents which can be admixed with at least one water soluble sugar in an amount of from 5 to 95 weight % of the total dosage form and at least one non-sugar sweetener in a fast release form in an amount of from 0 to 10 weight % of the total dosage form; and at least one non-sugar sweetener in a mucoadhesive slow release form in an amount of from 0.5 to 20 weight % of the total dosage form. The mixture can then be compressed into a tablet or other solid dosage form using known methods.

The active agents can also be in an encapsulated or microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agents may be admixed with at least one inert diluent such as sucrose, lactose or starch. Such dosage forms may also comprise additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner.

In one embodiment the active agents can be incorporated into liposomes by any known method and the liposomes can then be encapsulated in bead form. The beads can be formed by suspending the liposomes in a physical and potentially physiochemical bonding solution. The bonding solution can contain at least one organic compound such as agarose, cellulose, sodium alginate, chitosans, polymeric substances or other compounds with the necessary characteristic of physical or physiochemical bonding. This solution can then be introduced into a second solution containing from about 1 to 2% by weight of an inorganic salt. The effect of the interaction of the solutions is to harden the outer most exposed areas of the introduced liposome solution. The inorganic salt can be calcium chloride or sodium hydroxide, although other types of inorganic salts can be used such as calcium sulfate, calcium carbonate, magnesium chloride, magnesium sulfate, barium chloride, barium sulfate and the like.

Dosage forms for topical or transdermal administration of the active agents include ointments, pastes, creams, lotions, gels, powders, solutions, sprays, inhalants or transdermal patches. Additionally, the use of transdermal patches as are known. Transdermal patches have the added advantage of providing controlled delivery of active agents to the body. Such dosage forms can be made by dissolving or dispensing the active agents in a suitable medium as is known. Absorption enhancers can also be used to increase the flux of the active agents across the skin. The rate can be controlled by either providing a rate controlling membrane or by dispersing the active agents in a polymer matrix or gel. Eardrops and eye drops are also contemplated.

The compositions can be formulated in immediate release or sustained release formulations.

A sustained-release form is a form suitable for providing controlled-release of the ingredients in an aqueous medium over a sustained period of time (e.g., 8 hours, 12 hours, 24 hours). This provides for an increased duration of the ingredients allowing once-daily dosing. Such compositions can include a release-retarding material in the form of, for example, a matrix or a coating.

Numerous release-retarding materials are known and can be used. These include for example acrylic polymers, alkylcelluloses, shellac, zein, waxes, hydrogenated vegetable oil, hydrogenated castor oil as are known and their combinations. The oral dosage form can contain from about 1 wt. % to about 80 wt. % of the release-retarding material. Suitable acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly (methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, and combinations comprising one or more of the foregoing polymers. Suitable acrylic polymers include methacrylate copolymers as fully polymerized copolymers of acrylic and methacrylic acid esters with a low content of quaternary ammonium groups. Suitable alkylcelluloses include, for example, ethylcellulose. Those skilled in the art will appreciate that other cellulosic polymers, including other alkyl cellulosic polymers, can be substituted for part or all of the ethylcellulose.

The release-retarding material can also include other additives such as an erosion-promoting agent (e.g., starch and gums); and/or a semi-permeable polymer. In addition to the above ingredients, a sustained-release dosage form can also contain suitable quantities of other materials, e.g., diluents, lubricants, binders, granulating aids, colorants, flavorants and glidants that are conventional in the pharmaceutical art. The release-retarding material optionally includes an exit means comprising at least one passageway, orifice, or the like. The passageway can have a suitable shape, such as round, triangular, square, elliptical, irregular, etc.

Sustained release formulations can be incorporated into a dosage form that is mechanically stabilized to increase the difficulty of comminuting by conventional methods, such as pounding, crushing, grinding in a mortar etc. In such dosage forms the active agents can still release under physiological conditions with the intended delayed release profile. This can be helpful in maintaining the release profile of sustained release formulations when comminution would otherwise compromise the release characteristics by partially destroying the matrix controlling release and/or the film coating on the dosage form which controls release. Stabile dosage forms can be obtained by including a polymer polyalkylene oxide having a weight average molecular weight or viscosity average molecular weight of at least $0.5 \times 10^6$ g/mol in combination with at least one further polymer, preferably also having a weight average molecular weight (Mw) or viscosity average molecular weight of at least $0.5 \times 10^6$ g/mol, selected from the group consisting of polyethylene, polypropylene, polyvinyl chloride, polycarbonate, polystyrene, polyacrylate, poly(hydroxy fatty acids), polycaprolactone, polyvinyl alcohol, polyesteramide, polyethylene succinate, polylactone, polyglycolide, polyurethane, polyvinylpyrrolidone, polyamide, polylactide, polyacetal, polylactide/glycolide, polylactone, polyglycolide, polyorthoester, polyanhydride, block polymers of polyethylene glycol and polybutylene terephthalate, polyanhydride and copolymers thereof. The polymers preferably have a viscosity at 25° C. of 4,500 to 17,600 cP, measured in a 5 wt. % aqueous solution, of 400 to 4,000 cP, or of 1,650 to 10,000 cP, measured on a 1 wt. % aqueous solution. In general, the process for the production of the dosage form involves mixing the active agents with the polymer mixture and applying heat and/or force to the mixture to harden the mixture. The heat supplied should preferably not be sufficient to reduce the activity of the active agents. The mixture can be shaped as it hardens. Heat may be supplied directly or with the assistance of ultrasound. Force may be applied and/or the dosage form may be shaped for example by direct tabletting or with the assistance of a suitable extruder, particularly by means of a screw extruder equipped with two screws (twin-screw-extruder) or by means of a planetary gear extruder.

For the treatment of bruises daily doses may be given as a single administration (e.g. a daily tablet for oral consumption or as a single liquid drink). Alternatively the composition used may be administered twice or more times during a day.

It will also be appreciated that the disclosed active agents and pharmaceutical compositions can be employed in combination therapies, that is, the active agents and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved.

A method of reducing bruising is also disclosed in which a patient in need of a treatment for bruising or at risk of developing bruises is identified. The composition is then administered orally to the patient.

One representative formulation and its use in preventing and accelerating the healing of purpura bruises is set forth in the following example.

EXAMPLES

Example 1

Formulation

Table 1 shows a preferred formulation for the disclosed composition. One skilled in the art will recognize that alternate equivalent formulations are encompassed by this example.

TABLE 1

Formula I (tablet)

| Ingredient | Amount |
| --- | --- |
| Ascorbic acid | 250 mg |
| Rutin | 500 mg |
| Citrus bioflavinoids | 500 mg |
| Hesperidin | 50 mg |
| Eriocitrin | 50 mg |
| *Arnica montana* (30x) | 2 mg |
| Calcium (from calcium ascorbate) | 250 mg |

Example 2

Formula I reduces skin bruising and increases the rate of healing in patients with senile purpura.

Sixty-seven (67) patients were enrolled in a randomized, double-blind, placebo-controlled study. Thirty five (35) patients were treated by oral administration of a tablet having the ingredients listed in Formula I and thirty two (32) were treated with a placebo tablet made of calcium carbonate. Patients received one tablet twice daily. The number of purpura lesions on the forearms, hands, and/or legs were measured at two week intervals for six weeks. No serious adverse events or side-effects were noted in either the treated or placebo groups.

The speed of purpura lesion healing was measured by counting the number of lesions on the forearms, hands or legs for each patient. The results are shown as the percent change at baseline in the number of lesions at each two week interval. Then, the percent change from baseline was compared between groups. Data are reported as mean values (±standard error of the mean) in each example. Improvement in the number of purpura lesions was observed as early as one week after treatment and significant improvement was detected after 6 weeks of treatment (FIG. 1). Specifically, the number of purpura bruises decreased by 19% (±9.8) at two weeks, 29% (±10.2) at 4 weeks and 50% (±7.8) at 6 weeks (p=0.02) in the treated patients (n=35) while a 9% (±23.7) increase was observed at 6 weeks in the placebo-treated group (n=32) compared to baseline. Additionally, the treatment prevented new lesions from appearing while the placebo group showed a 9% increase in lesions at 6 weeks.

Figure 2:
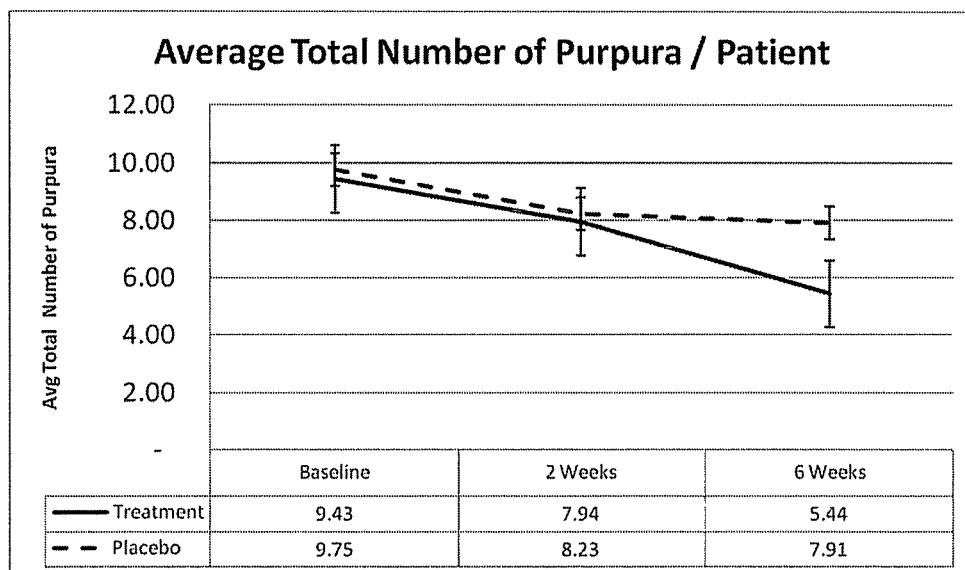
FIG. 2 shows the average number of purpura per patient in the treatment and placebo groups at baseline and 2 and 6 weeks post-treatment.

The average number of purpura lesions per patient continued to decline with treatment (n=35) compared to the placebo (n=32) group. The total number of lesions on the forearms, hands and legs of all patients were counted and compared post-treatment at 2-week intervals. Twice daily treatment with Formula I significantly reduced the total number of purpura lesions in the treated group (n=35) from 9.43 (±1.56) at baseline to 5.44 (±1.25; p=0.02) at six weeks compared to the control group (n=32; 9.75 (±1.92), baseline; 7.91 (±1.86), at six weeks). These results are shown in FIG. 2.

Next, the average rate of healing, defined as the disappearance of purpura, was assessed for each patient post-treatment at each two week interval. The total number of purpura was computed for each group and the percent change from baseline and the average number of lesions for all three 2-week intervals for the treated and placebo groups were compared. In other words, the average number of lesions was calculated from the average change from baseline to 2 weeks, 2 to 4 weeks and 4 to 6 weeks. The average number of purpura (<3 cm) significantly decreased 133% faster (p=0.05) than the placebo group. The average 2 week change in the total number of purpura was significantly reduced by 13% (±11.0; p=0.05) in the treated group compared to a 40% (±25) increase in the placebo group. These results indicate that twice daily treatment with Formula I leads to a markedly faster speed of purpura healing compared to placebo.

Lastly, each patient's perception of the purpura healing was also evaluated weekly for each group. Patients were asked how they felt about the appearance of the bruises under examination in the study. A score ranging from 0 to 10 was possible from each patient. A score of 0 indicated that the patient felt the bruises were much worse while a score of 10 indicated that the patient felt the bruises were much better and a score of 5 indicated that the patient did not think the bruises had changed. Patients in the treatment group scored consistently higher on the survey compared to the placebo group indicating an improvement in purpura healing over the course of the study. The average score for each week was as follows: 8.4 (7.9) for week 1, 9.2 (8.9) for week 2, 8.6 (8.1) for week 3, 8.8 (8.2) for week 4, 8.6 (8.1) for week 5, and 8.5 (8.3) for week 6 in the treated group (and placebo group).

Figure 3:
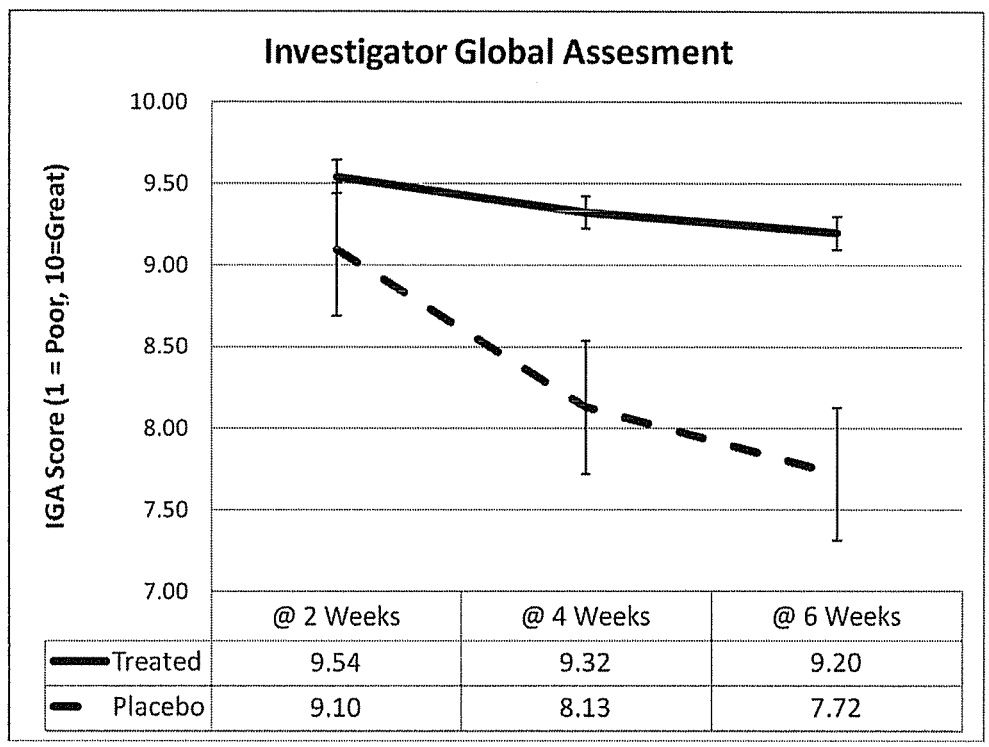
FIG. 3 shows the Investigator Global Assessment scores at each 2 week treatment interval for the treatment and placebo groups.

An Investigator Global Assessment (IGA) score measuring improvement of the appearance of purpura was also determined for each patient post-treatment at two week intervals over the six week study. For this assessment the investigators were asked to evaluate whether their patient's bruises were improving with a score from 1 to 10 with 10 indicating the most improved healing. FIG. 3 shows that after 6 weeks, the IGA scores significantly improved in the treated patients at 9.2 (±0.51), compared to 7.7 (±0.45) for the placebo group (p=0.03). Additionally, the placebo group showed a significant decrease (p=0.01) in IGA at each 2 week assessment, indicating a worsening of the appearance of purpura. These results parallel the patients' own assessment of their healing.

In summary these examples show that 6 weeks of treatment with Formula I reduced purpura by 50% compared to baseline in the treatment group. Treatment with Formula I also prevented the formation of new purpura lesions and improved the appearance of purpura as early as 1 week after starting treatment. These results were further supported by the IGA scores.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

This application claims benefit of U.S. Provisional Patent Application Ser. Nos. 61/349,335 filed May 28, 2010 and 61/364,033 filed Jul. 14, 2010.

What is claimed is:

1. A method of reducing bruising, the method comprising: (a) identifying a patient who has bruises; and (b) administering to the patient a pharmaceutical composition comprising ascorbic acid, a water soluble ester of ascorbic acid, calcium ascorbate, or a lipophilic ester of ascorbic acid; rutin; hesperidin; eriocitrin; and a pharmaceutically acceptable excipient, wherein the amount of the composition administered is sufficient to reduce the healing time of the bruises and wherein the patient is one who is being treated with an anticoagulant medication or who has senile purpura, a coagulation disorder, capillaritis, pigmented purpuric dermatosis, Schamberg's disease, or a connective tissue disorder.

2. The method of claim 1, wherein the composition is administered by one or more of the following routes of administration: oral, buccal, sublingual, sublabial, nasal inhalation, urogenital, intravesicular, intravaginal, rectal, transdermal, subcutaneous, intravenous, or intramuscular.

3. The method of claim 1, wherein the composition is administered orally.

4. The method of claim 1, wherein the composition is administered topically.

5. The method of claim 1, wherein the composition is administered transdermally.

6. The method of claim 2, wherein oral administration comprises administering a tablet or capsule dosage form one or more times per day.

7. The method of claim 1, wherein the composition further comprises calcium carbonate, an extract of *Arnica montana*, vitamin K, folic acid, *Croton lechleri* extract, or *Aspilia africana* extract.

8. The method of claim 1, wherein the excipient comprises a dispersion or suspension aid, a surface active agent, a thickening or emulsifying agent, a preservative, or a lubricant.

9. The method of claim 1, wherein the excipient comprises cocoa butter, polyethylene glycol or a suppository wax.

10. The method of claim 1, wherein the coagulation disorder is hemophilia, von Willebrand's disease, or Factor V Leiden deficiency.

11. The method of claim 1, wherein the connective tissue disorder is Ehlers-Danlos Syndrome.

12. A method of reducing bruising, the method comprising administering to a patient who has bruises a pharmaceutical composition consisting of ascorbic acid, a water-soluble ester of ascorbic acid, calcium ascorbate, or a lipophilic ester of ascorbic acid, rutin, hesperidin, eriocitrin, an extract of *Arnica montana*, and one or more pharmaceutically acceptable excipients, wherein the amount of the composition administered is sufficient to reduce the healing time of the bruises.

13. The method of claim 12, wherein the method comprises a step of identifying a patient in need of a treatment for bruising prior to administering the composition.

* * * * *